United States Patent
Hsueh et al.

(10) Patent No.: US 7,811,230 B2
(45) Date of Patent: Oct. 12, 2010

(54) EXPANSION MECHANISM FOR MINIMALLY INVASIVE LUMBAR OPERATION

(75) Inventors: Shao-Kang Hsueh, 3F-1, No. 445, Guangfu S. Rd., Sinyi District, Taipei City 110 (TW); Jen-Kun Chang, Yangmei Township, Taoyuan County (TW); Chen-Yu Lung, Taipei (TW)

(73) Assignees: United Orthopedic Corporation, Hsinchu (TW); Shao-Kang Hsueh, Taipei (TW)

( * ) Notice: Subject to any disclaimer, the term of this patent is extended or adjusted under 35 U.S.C. 154(b) by 783 days.

(21) Appl. No.: 11/713,096

(22) Filed: Mar. 2, 2007

(65) Prior Publication Data

US 2008/0215081 A1 Sep. 4, 2008

(51) Int. Cl.
*A61B 1/32* (2006.01)
(52) U.S. Cl. .................. 600/215; 600/210; 600/235
(58) Field of Classification Search .................. 74/535, 74/537, 575, 577 M, 577 R; 248/292.12, 248/354.7; 600/201–246; 606/191, 201
See application file for complete search history.

(56) References Cited

U.S. PATENT DOCUMENTS

| | | | | |
|---|---|---|---|---|
| 3,522,799 | A * | 8/1970 | Gauthier | 600/215 |
| 3,749,088 | A * | 7/1973 | Kohlmann | 600/215 |
| 4,421,107 | A * | 12/1983 | Estes et al. | 600/206 |
| 4,421,108 | A * | 12/1983 | Cabrera et al. | 600/234 |
| 5,755,660 | A * | 5/1998 | Tyagi | 600/205 |
| 7,435,219 | B2 * | 10/2008 | Kim | 600/233 |
| 2006/0224044 | A1 * | 10/2006 | Marchek et al. | 600/233 |

* cited by examiner

*Primary Examiner*—Thomas C Barrett
*Assistant Examiner*—Larry E Waggle, Jr.
(74) *Attorney, Agent, or Firm*—Muncy, Geissler, Olds & Lowe, PLLC

(57) ABSTRACT

An expansion mechanism for minimally invasive lumbar operation has a support member, a plurality of sliders movably assembled on the support member, at least a couple of outside muscle hook members mounted on adjacent sliders, an inside muscle hook member assembled on the slider, and a nerve hook member assembled on the slider. The expansion mechanism for minimally invasive operation makes small incisions and hurts less tissues. Furthermore, the expansion mechanism protects nerve tissues from repeated stirring. Muscles can be drawn apart without the need of removing ligament, obtaining clear and large operation vision.

19 Claims, 14 Drawing Sheets

US 7,811,230 B2

EXPANSION MECHANISM FOR MINIMALLY INVASIVE LUMBAR OPERATION

BACKGROUND OF THE INVENTION (a) Field of the Invention

The present invention relates to an expansion mechanism for minimally invasive lumbar operation, and particularly to an expansion mechanism for minimally invasive lumbar operation which protects nerve tissues in operations and makes small incisions.

(b) Description of the Prior Art

Lumbar deteriorations, such as vertebra stenosis, herniated disc etc., often lead to serious sciatica, claudication or nerve degeneration. Some of the patients have to be treated surgically, but always hesitate to be further treated surgically after long-term restoration and recurrence. In a traditional operation, as shown in FIGS. 1 and 2, fascia and supraspinous ligament is cut along a middle of a patient's back. Muscles 41 surrounding a vertebra 4 are poked along a periosteum by a tool 42, and are anchored at opposing sides by a hook 43. Ligament adhered to the vertebra 4 have to be ruled out. A traditional surgery laminectomy needs to remove spines and interspinous ligament to abirrate nerves. This process may damage partial vertebra, muscles, and spines. In general, this process has following deficiencies:

1. Even if the muscles have been sutured, the muscles and the spines can not recover as they should be originally and are inconsistent with physical back muscles.

2. dead space is excessively large, taking a risk of epidural fibrosis thereby influencing treatment effect.

3. supraspinous ligament, spines and interspinous ligament are removed, tending to make the spinal column instable.

The traditional operation has much shortcomings, and correspondingly, a minimally invasive operation which makes small incisions and damages minimum tissues is advanced. Currently, such a minimally invasive operation is normally called endoscopic treatment, as shown in FIG. 3. In the endoscopic treatment, a sleeve 5 with a diameter about 2 cm is pulled through muscles 52 around a vertebra 51. A miniature camera 53 is put on the sleeve 5. Vision is projected on a display screen (not shown). Tools 55 are provided on the sleeve 5 for performing the operation. The operation makes small incisions and damages minimum tissues, and thus overcoming the shortcomings above.

However, as for minimally invasive operations, when the sleeve 5 extends through the muscles 52 around the vertebra 51 and reaches a predetermined location, an end of the sleeve 5 is bound by the profile of the vertebra 51. During operation, only a vision within the sleeve 5 of about 2 cm is provided. Moreover, tools 55 are extended through the sleeve 5, and accordingly form some dead angles of vision. Thus nerves can not be abirritated enough, and thus such an operation is difficult to perform.

SUMMARY OF THE INVENTION

Accordingly, an object of the present invention is to provide an expansion mechanism for minimally invasive lumbar operation, which makes small incisions and hurts less tissues during minimally invasive operations, and which protects nerve tissues from repeated stirring, and draws muscles apart in the case the ligament are not ruled out, forming clear and relatively large operation vision.

An expansion mechanism for minimally invasive lumbar operation in accordance with the present invention comprises a support member, a plurality of sliders, at least a couple of outside muscle hook members, an inside muscle hook member assembled on the slider, and a nerve hook member assembled on the slider. The support member includes an annular guiding track. The sliders are movably assembled on the annular guiding track. The outside muscle hook members are mounted on adjacent sliders.

DETAIL DESCRIPTION OF THE PREFERRED EMBODIMENTS

Figure 1:
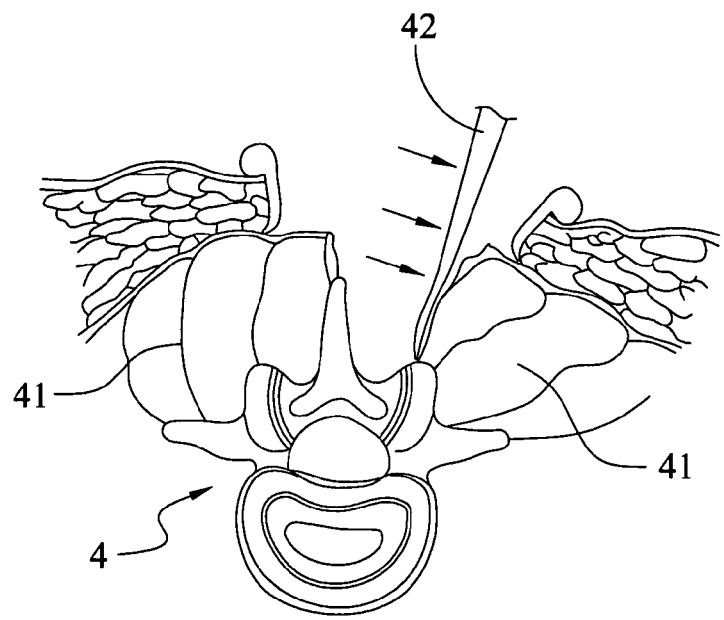
FIGS. 1 and 2 schematically show a traditional lumbar operation.
Figure 2:
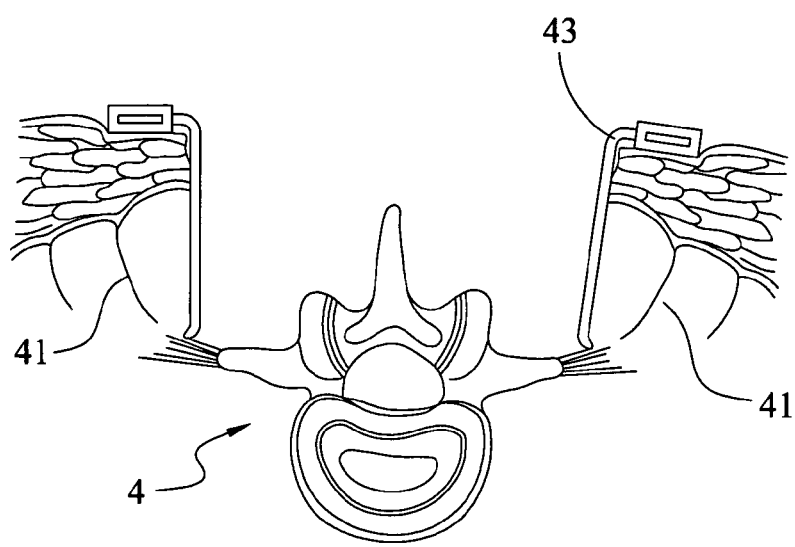
Figure 3:
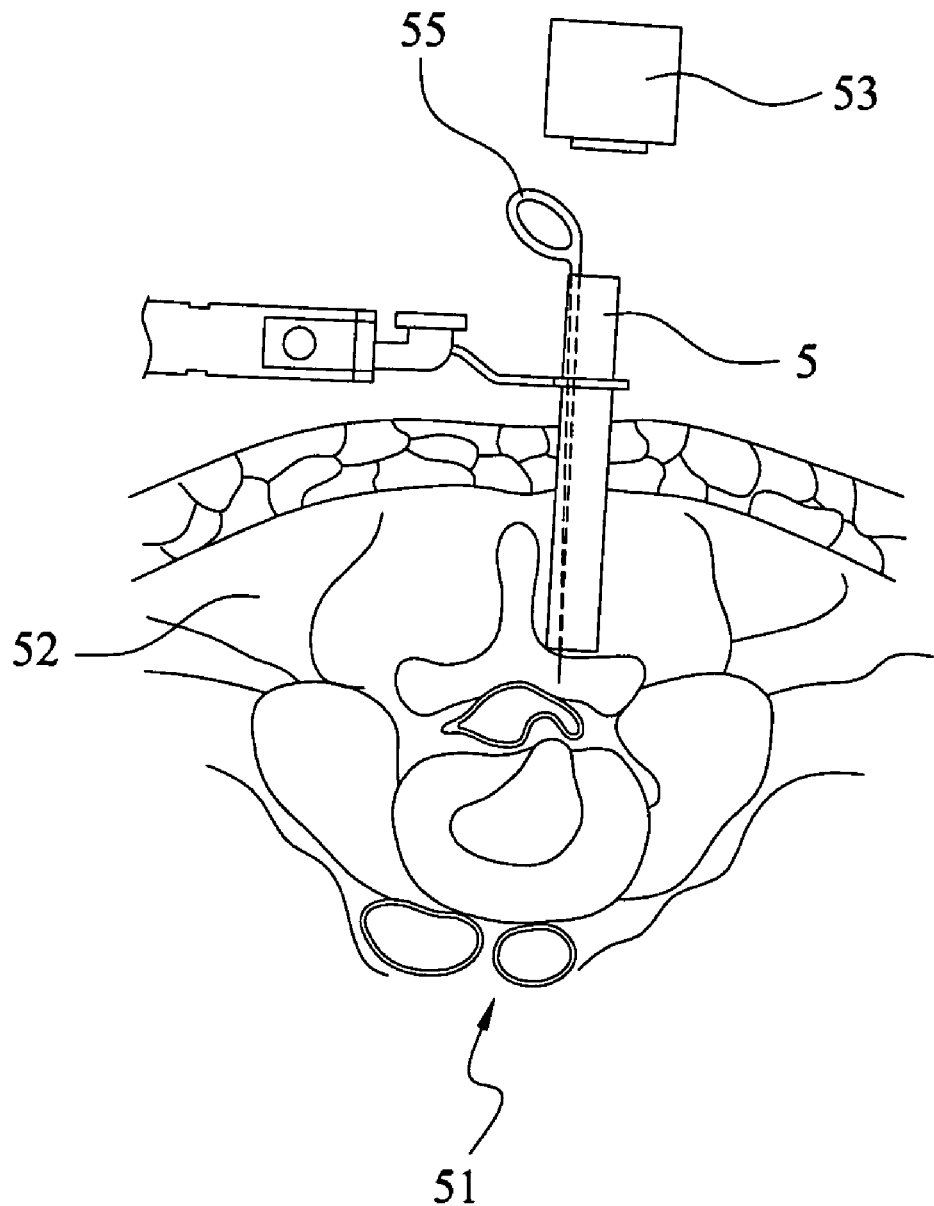
FIG. 3 schematically shows a minimally invasive lumbar operation.
Figure 4:
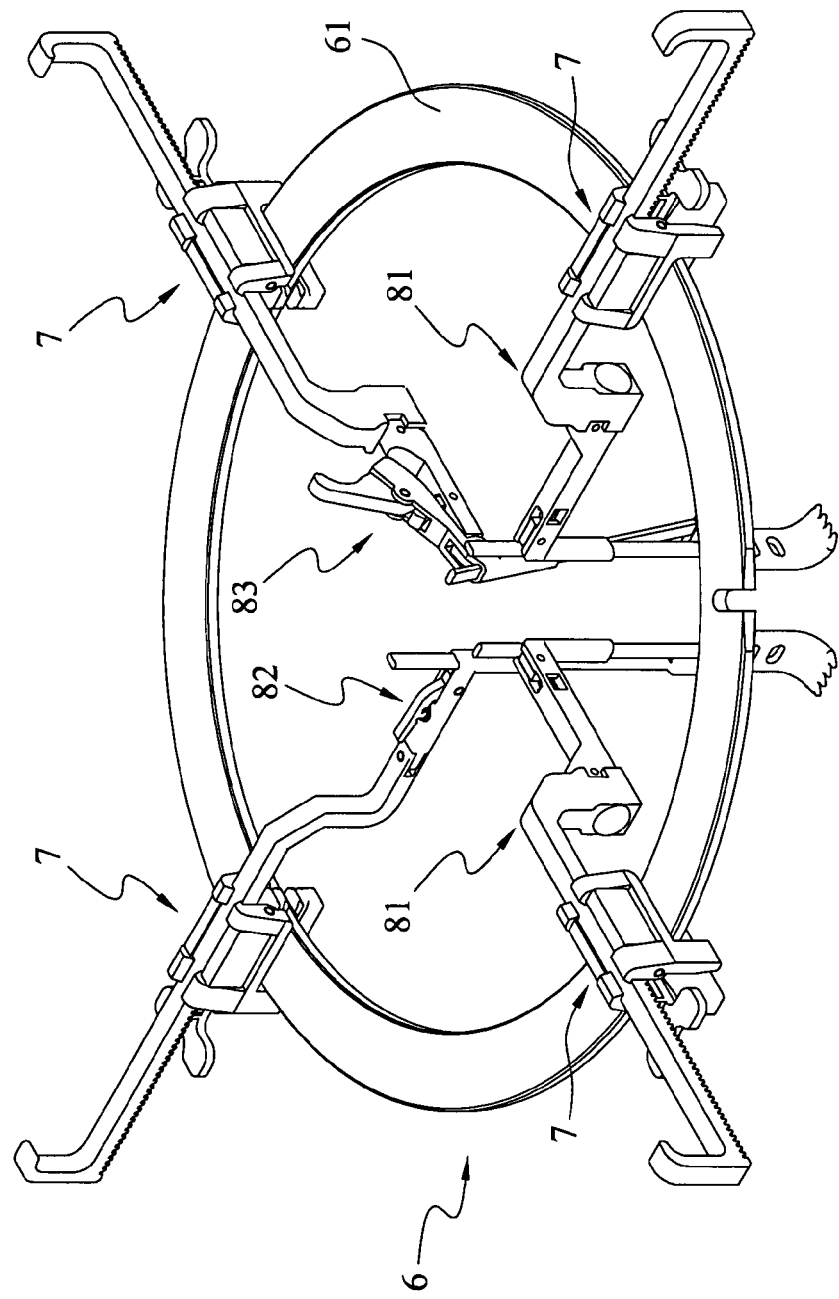
FIG. 4 is a perspective view of an expansion mechanism for minimally invasive lumbar operation according to the present invention.
Figure 5:
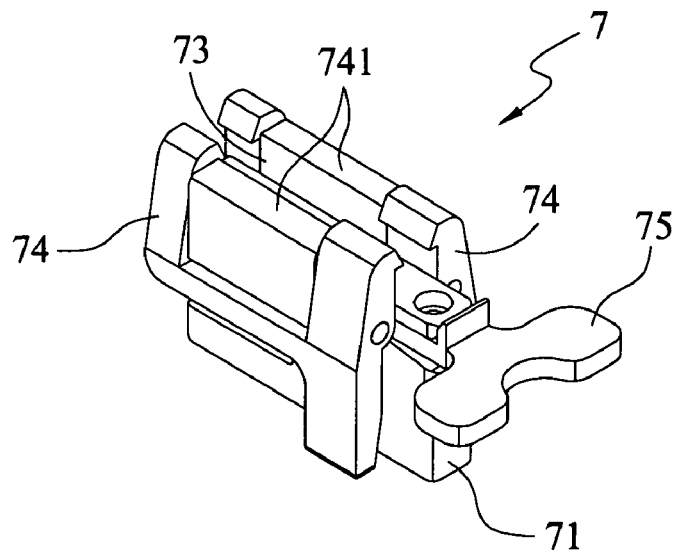
FIG. 5 is a perspective view of a slider of the expansion mechanism for a minimally invasive lumbar operation.
Figure 6:
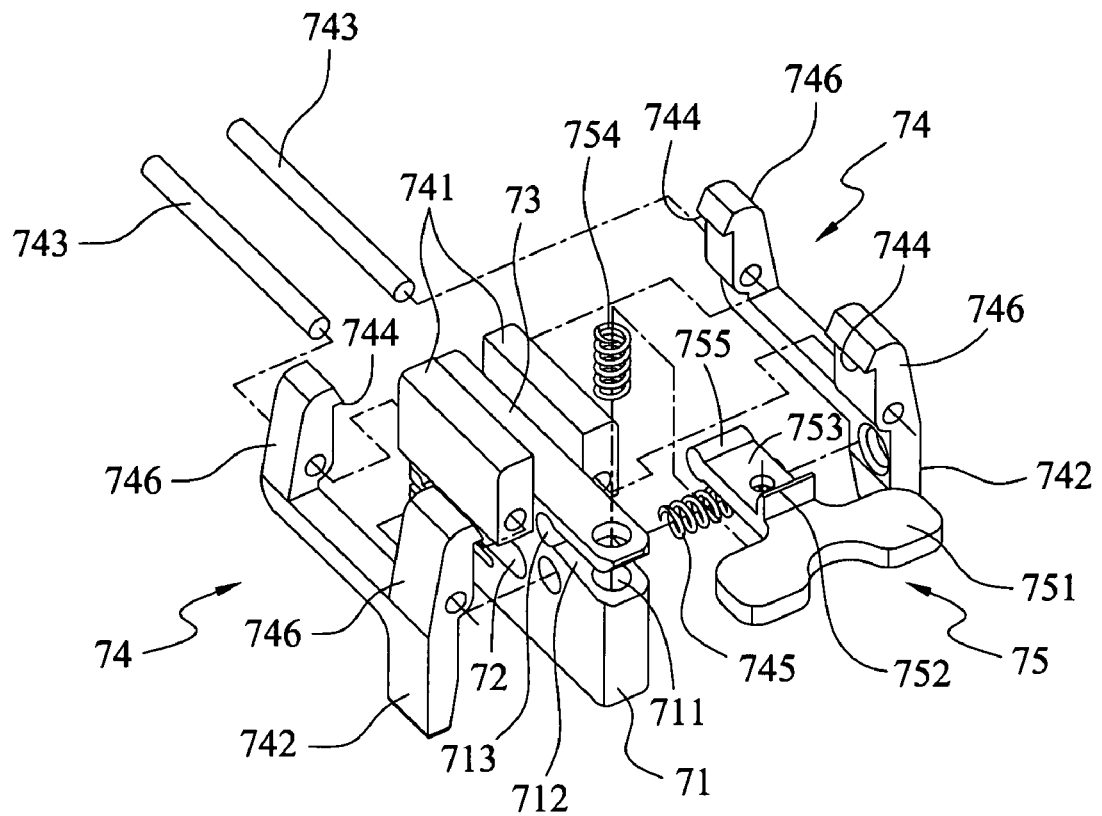
FIG. 6 is an exploded view of the slider of FIG. 5.

With reference to FIGS. 4 to 19, an expansion mechanism for minimally invasive lumbar operation according to the present invention comprises a support member 6, a plurality of sliders 7, at least a couple of outside muscle hook members 81, an inside muscle hook member 82 and a nerve hook member 83.

The support member 6 includes an annular guiding track 61 with an outer diameter of 20 cm, which is fixed on an operation table (not shown) by support arms (not shown).

Figure 7:
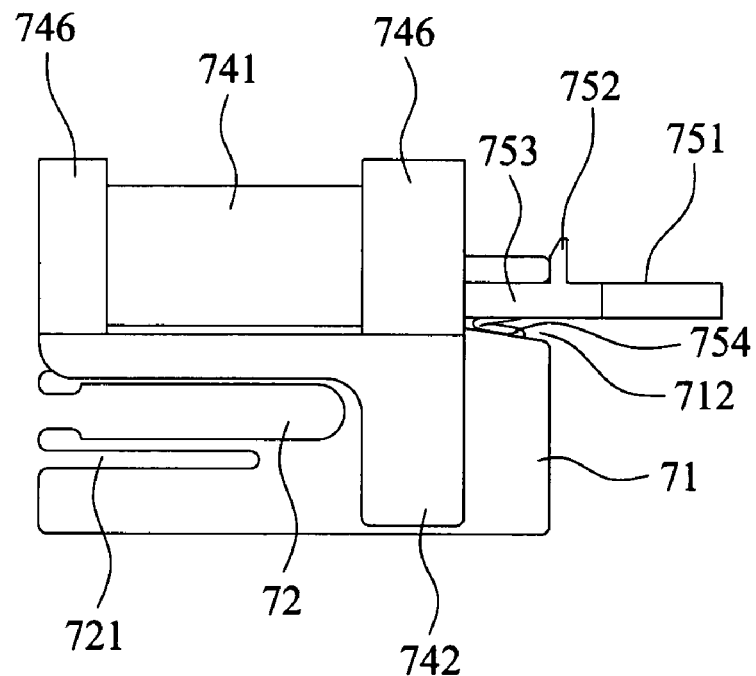
FIG. 7 is a side view of the slider of FIG. 5.
Figure 8:
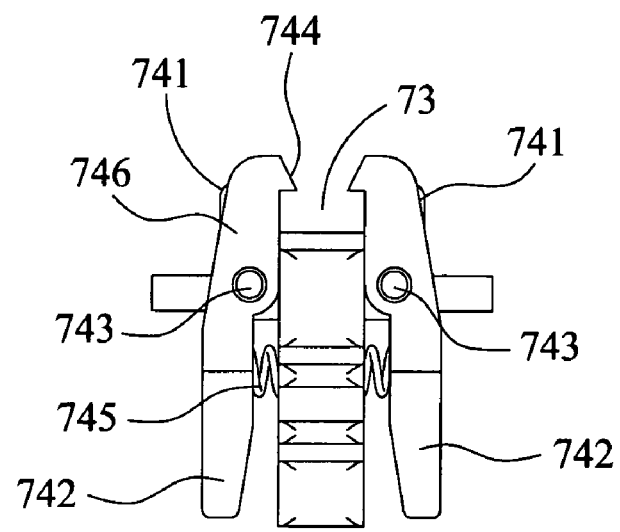
FIG. 8 is a front view of the slider of FIG. 5.
Figure 9:
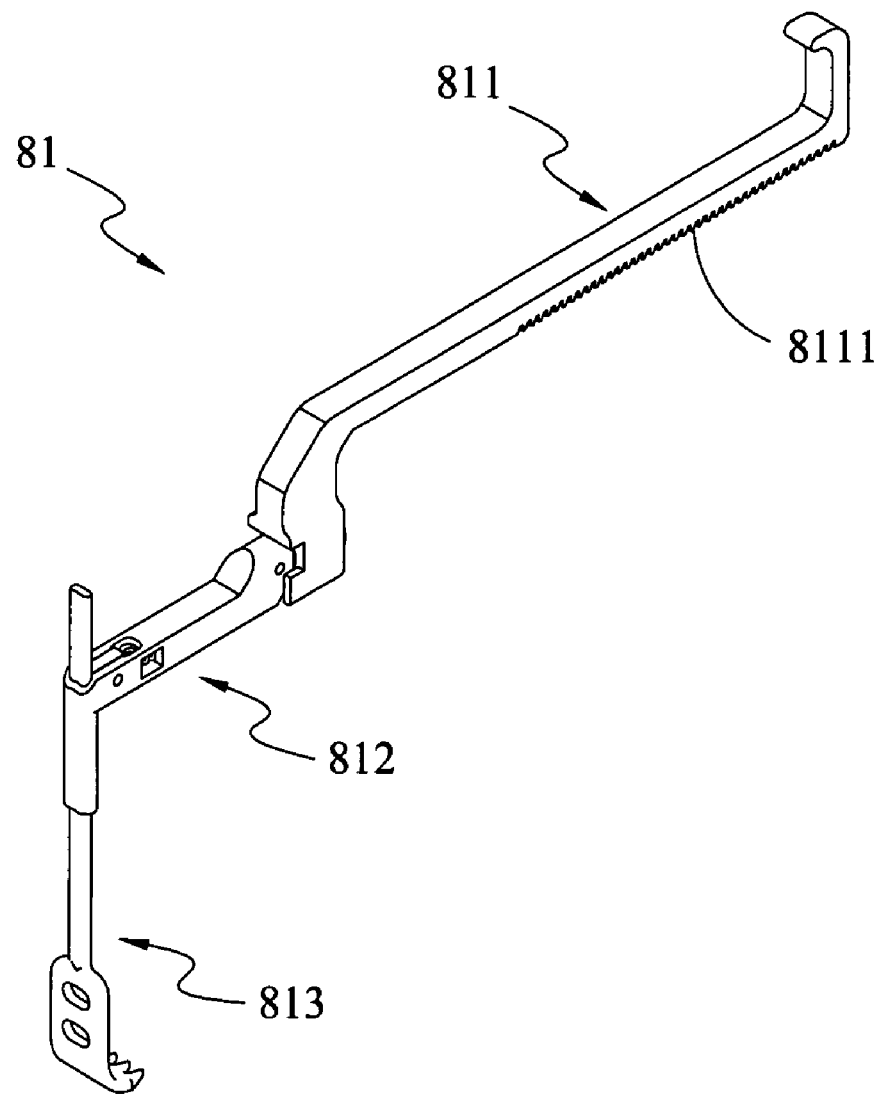
FIG. 9 is a perspective view of an outside muscle hook member of the expansion mechanism for a minimally invasive lumbar operation.
Figure 10:
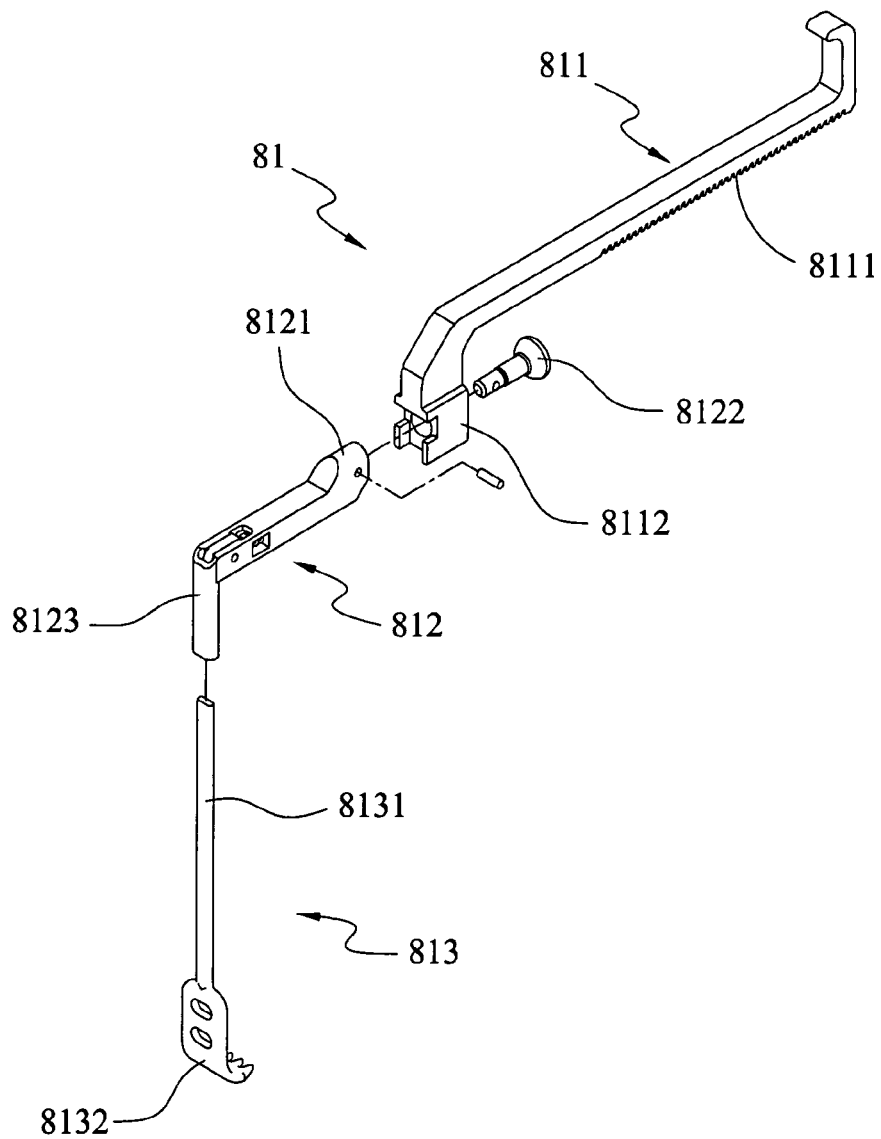
FIG. 10 is an exploded view of the outside muscle hook member of FIG. 9.
Figure 11:
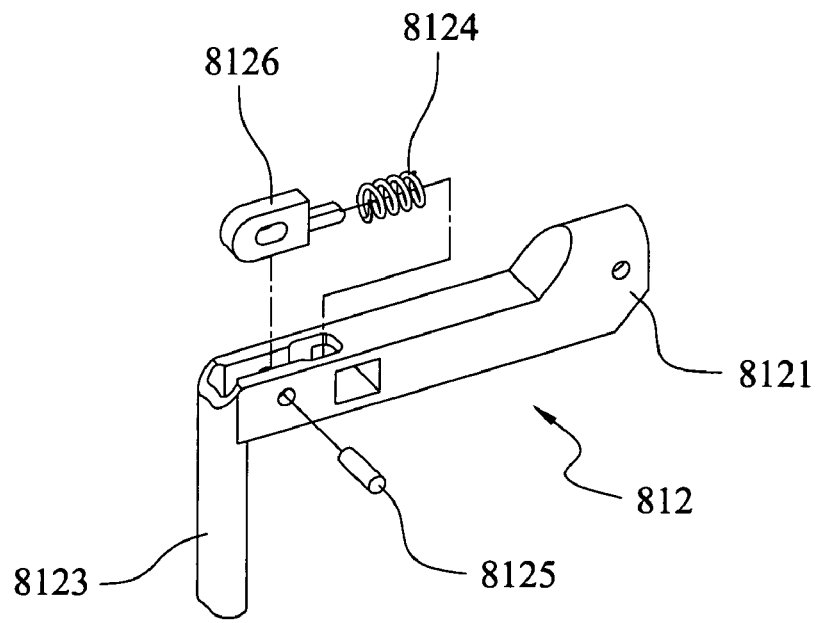
FIG. 11 is an exploded view of a first connecting unit of the outside muscle hook member.
Figure 12:
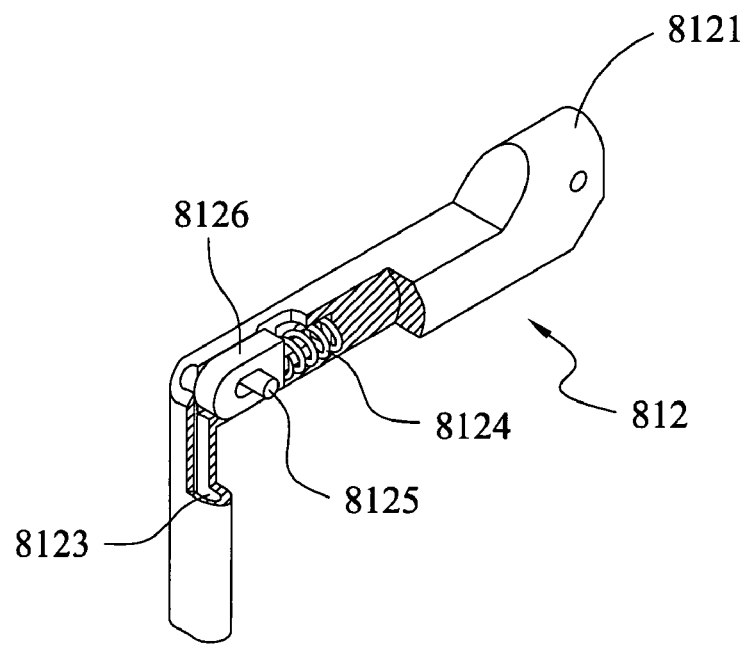
FIG. 12 is a partially cross-sectional view of the first connecting unit of FIG. 11.

The sliders 7 are movably assembled on the annular guiding track 61. Referring to FIGS. 5 to 8, each slider 7 includes a base 71 with an assembling portion 72 therein. For instance, the assembling portion 72 is a lateral U-shaped slot. The assembling portion 72 is movably mounted on the annular guiding track 61, and therefore, the slider 7 is optionally movable on the annular guiding track 61 and is able to be fixed at any position. Stopping portions 741 are formed on opposing sides of the base 71 and define an elongated groove 73 therebetween. Limiting portions 74 are pivoted to opposite sides of the stopping portions 741. A wedged groove 712 is defined in the base 71, and an adjusting portion 75 is assembled in the wedged groove 712. Each limiting portion 74 has a pair of latches 746 extending upwardly. A pair of connecting bars 743 respectively pivots the latches 746 to the stopping portions 741. Projections 744 respectively extend inwardly from tops of the latches 746 for limiting the elongated groove 73. Each limiting portion 74 further has abutting portions 742 depending downwardly and inclined outwardly. A first spring 745 extends transversely through the base 71 and has two ends respectively abutting against the abutting portions 742. The projections 744 extend inwardly into the elongated groove 73 for limiting the elongated groove 73. The abutting portions 742 expand outwardly, as shown in FIG. 8. When the abutting portions 742 are pressed inwardly, the latches 746 expand outwardly and release limitation to the elongated groove 73. The adjusting portion 75 comprises a pressing portion 751, a biasing portion 752 extending upwardly from an end of the pressing portion 751, a pressing plate 752 extending backward from the pressing portion 751, and a second spring 754. The second spring 754 is extended into between a spring hole 711 of the base 71 and the pressing plate 753. The pressing plate 753 is received in the wedged groove 712 of the base 71. A post 755 extends from a distal end of the pressing plate 753 and is finally wedged into a C-shaped groove 713 in an end of the wedged groove 712. A bottom of the wedged groove 712 is slanted, whereby the pressing portion 751 can be pressed downwardly, and the biasing portion 752 can move downwardly, correspondingly. In assembly, the second spring 754 provides return force, and the biasing portion 752 remains to abut against the second spring 754, as shown in FIG. 7. A slit 721 is defined below the assembling portion 72 for providing resilient force, whereby the assembling portion 72 is readily assembled on the annular guiding track 61.

The sliders 7 essentially have two functions: 1) the sliders 7 may be mounted at any position of the annular guiding track 61; 2) a variety of hook members are able to be easily assembled.

At least a couple of outside muscle hook members 81 cooperates to draw multifidus muscles apart. The outside muscle hook members 81 are mounted on adjacent sliders 7. Referring to FIGS. 9 to 12, each outside muscle hook member 81 mainly comprises a first bracket 811 mounted on the slider 7, a first connecting unit 812 connecting with the first bracket 811, and an outside muscle hook 813 formed on the first connecting unit 812. The first bracket 811 is pulled through the elongated groove 73, and is retained by the projections 744 of the latches 746. A first indented surface 8111 is formed on a bottom of the first bracket 811 for interferentially engaging with the biasing portion 752. A first engaging portion 8112 is formed at an end of the first bracket 811. A first connecting portion 8121 of the first connecting unit 812 connects with the first engaging portion 8112 of the first bracket 811 by a versatile first connector 8122. The first connector 8122 is omni-directionally rotatable. Thus the first connecting unit 812 is allowed to be adjusted angularly with respect to the first bracket 811. A first sleeve portion 8123 is formed at an end of the first connecting unit 812. Further referring to FIGS. 11 and 12, a top block 8126 is provided on a top of the first sleeve portion 8123 and is brought into the first connecting unit 812. A third spring 8124 pushes the top block 8126 toward the sleeve portion 8123. A pivoting bar 8125 pivots the top block 8126 to the first connecting unit 812 for limiting movement of the top block 8126. The outside muscle hook 813 includes a first rod 8131, and an outside hook portion 8132 at an end of the first rod 8131. The first rod 8131 extends into the first sleeve portion 8123 and abuts the top block 8126.

Figure 13:
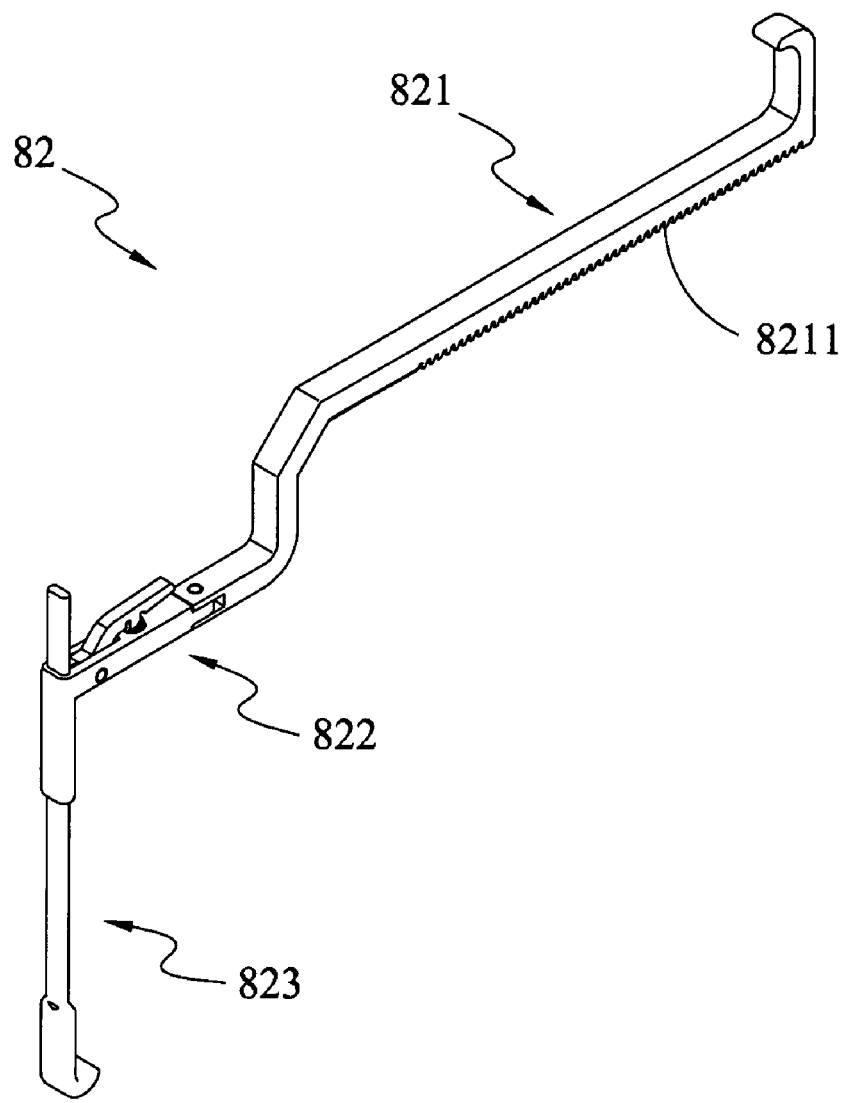
FIG. 13 is a perspective view of an inside muscle hook member of the expansion mechanism for a minimally invasive lumbar operation.
Figure 14:
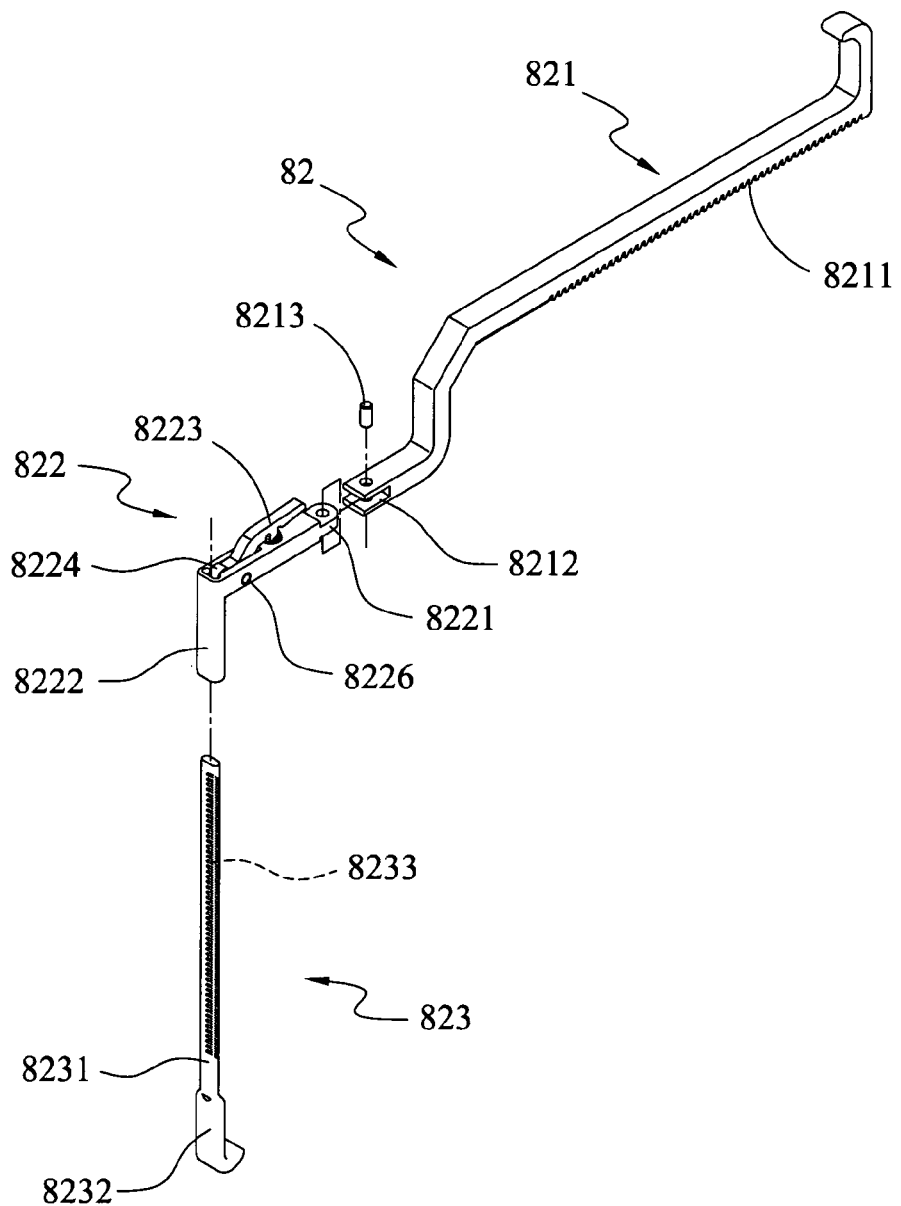
FIG. 14 is an exploded view of the inside muscle hook member of FIG. 13.
Figure 15:
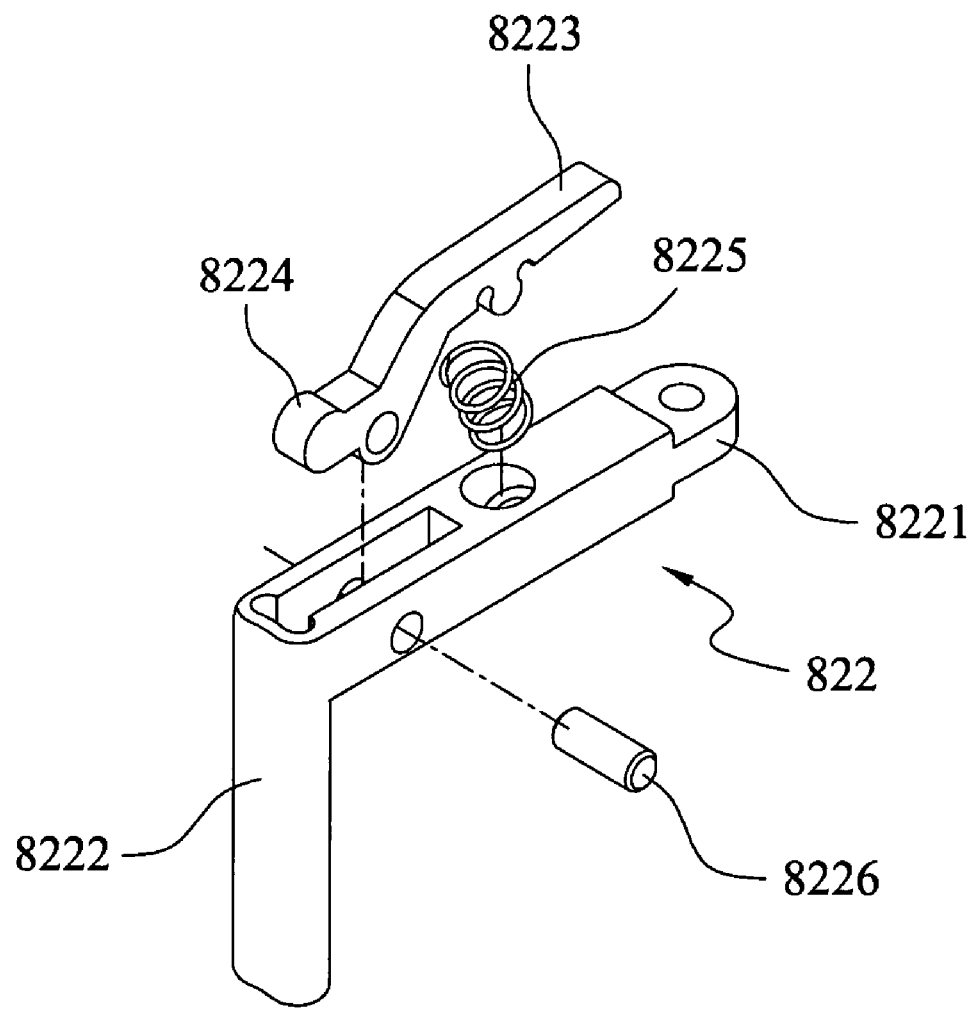
FIG. 15 is an exploded view of a second connecting unit of the inside muscle hook member.
Figure 16:
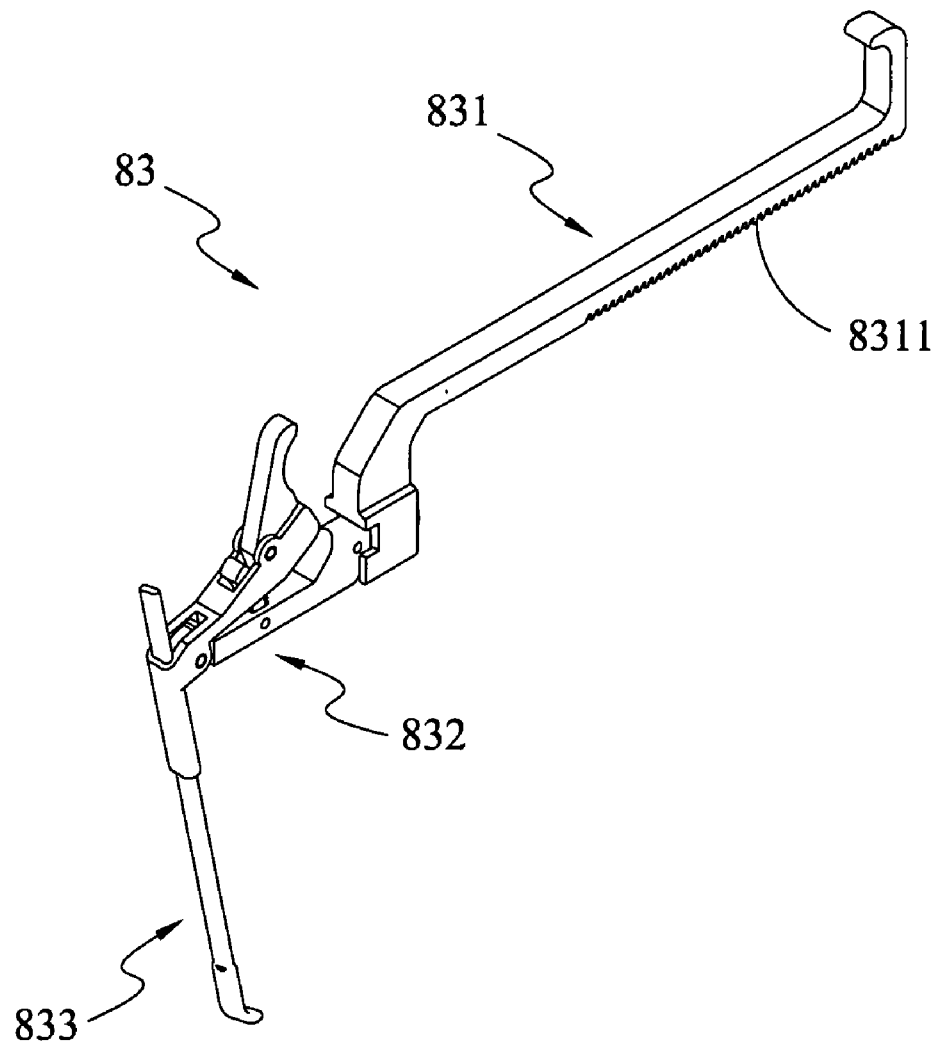
FIG. 16 is a perspective view of a nerve hook member of the expansion mechanism for a minimally invasive lumbar operation.
Figure 17:
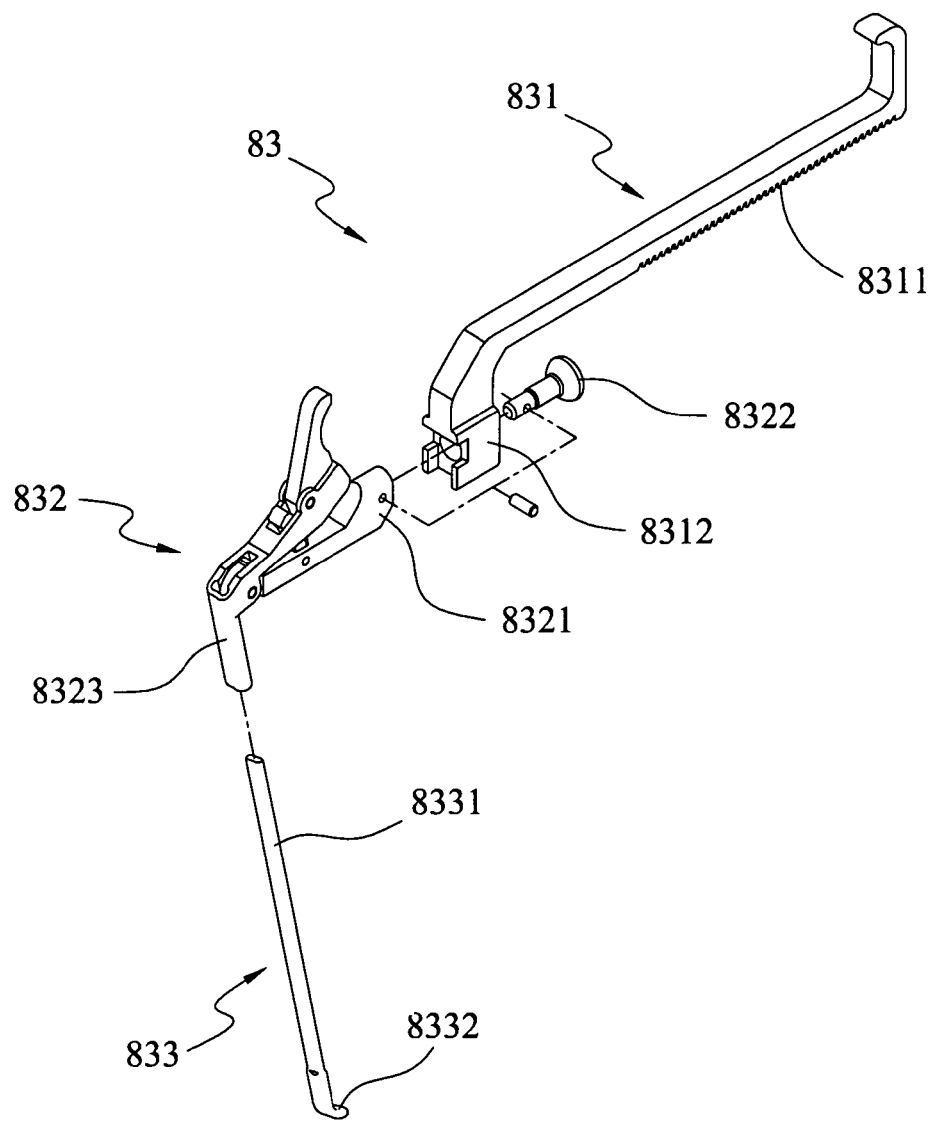
FIG. 17 is an exploded view of the nerve hook member of FIG. 16.

Referring to FIGS. 13 and 14, the inside muscle hook member 82 is assembled on the slider 7, and comprises a second bracket 821 assembled on the slider 7, a second connecting unit 822 connecting with the second bracket 821, and an inside muscle hook 823 formed on the second connecting unit 822. The inside muscle hook 823 is used to draw apart multifidus muscles within an operation vision, thereby enlarging the operation vision. As for patients with narrow vertebra, the inside muscle hook member 82 decreases pressure on the central canal. The second bracket 821 is pulled through the elongated groove 73, and is limited by the projections 744 of the latches 746. A second indented surface 8211 is formed on a bottom of the second bracket 821 for interferentially engaging with the biasing portion 752 of the slider 7. A second engaging portion 8212 is formed at an end of the second bracket 821. A second connecting portion 8221 of the second connecting unit 822 connects with the second engaging portion 8212 of the second bracket 821 by a pivoting shaft 8213. Thus the second connecting unit 822 is free in horizontal direction with respect to the first bracket 811. A second sleeve portion 8222 is formed at an end of the second connecting portion 8221 of the second connecting unit 822. A pressing section 8223 is movably mounted on the second connecting portion 8221 by a pivoting lever 8226. An abutting block 8224 is formed on an end of the pressing section 8223 and is accommodated in the second sleeve portion 8222. A resilient element 8225 is provided between the pressing section 8223 and the second connecting portion 8221. The inside muscle hook 823 includes a second rod 8231 connecting with the second connecting unit 822, and an inside hook portion 8232 at an end of the second rod 8231. A toothed portion 8233 is formed on a surface of the second rod 8231. Further referring to FIG. 15, the pivoting lever 8226 extends through the pressing section 8223. Consequently, when the pressing section 8223 is free, the pressing section 8223 pushes the abutting block 8224 toward the second sleeve portion 8222. The abutting block 8224 abuts against the toothed portion 8233 of the second rod 8231. The pressing section 8223 releases pressure of the abutting block 8224 upon the inside muscle hook 823. Therefore, the inside muscle hook 823 tends to move upwardly. The second rod 8231 of the inside muscle hook 823 extends into the second sleeve portion 8222. The abutting block 8224 abuts the inside muscle hook 823 and tends to bring the inside muscle hook 823 upwardly.

Figure 18:
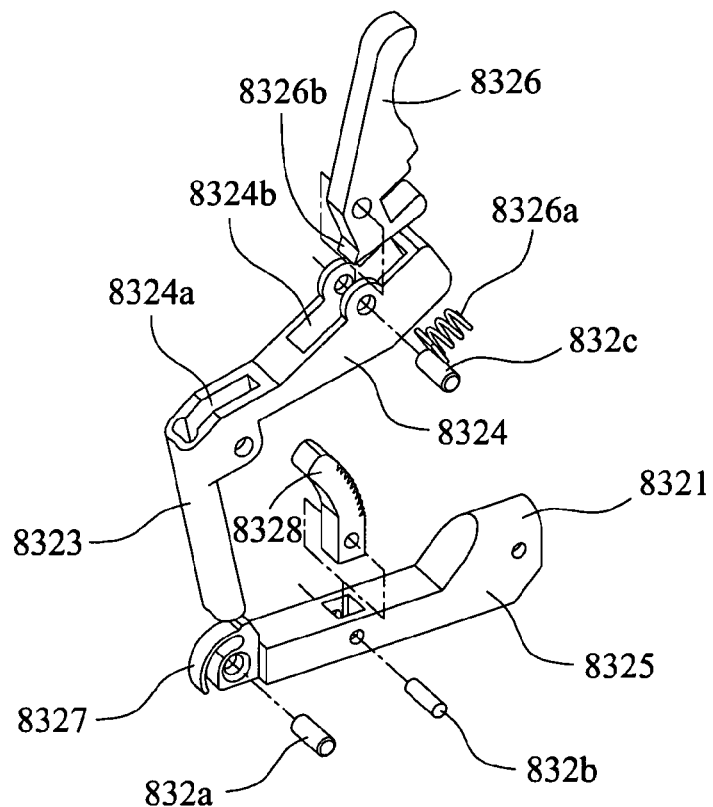
FIG. 18 is an exploded view of a third connecting unit of the nerve hook member.
Figure 19:
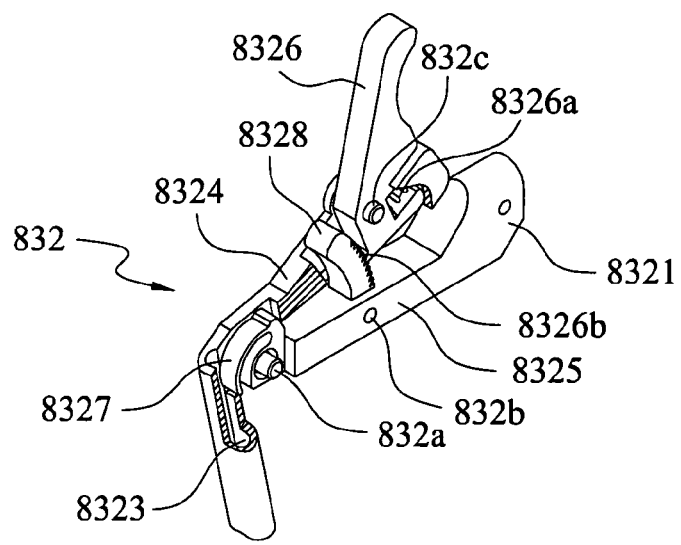
FIG. 19 is a partially cross-sectional view of the third connecting unit of FIG. 18.

Referring to FIGS. 16 to 19, the nerve hook member 83 is assembled on the slider 7, and mainly comprises a third bracket 831 assembled on the slider 7, a third connecting unit 832 connecting with the third bracket 831, and a nerve hook 833 formed on the third connecting unit 832. The nerve hook member 83 is used to draw apart and position neurofibrils once, and correspondingly avoiding repeated stir. The third bracket 831 is pulled through the elongated groove 73, and is limited by the projections 744 of the latches 746. A third indented surface 8311 is formed on a bottom of the third bracket 831 for interferentially engaging with the biasing portion 752 of the slider 7. A third engaging portion 8312 is formed at an end of the third bracket 831. A third connecting portion 8321 of the third connecting unit 832 connects with the third engaging portion 8312 of the third bracket 831 by a versatile second connector 8322. As thus the third connecting unit 832 is free in a horizontal direction with respect to the third bracket 831. A third sleeve portion 8322 is formed at an end of the third connecting unit 832. Referring to FIGS. 18 and 19, an upper section 8324 extends from a top of the third sleeve portion 8323, and a lower section 8325 extends from the third connecting portion 8321. A front opening 8324a is defined in the upper section 8324 and communicates with a top of the third sleeve portion 8323. A front end of the lower section 8325 is extended into the front opening 8324a. A first connecting shaft 832a extends into the front opening 8324a, and pivots the lower section 8325 onto the front opening 8324a of the upper section 8324. The nerve hook 833 includes a third rod 8331 and a nerve hook portion 8332 at an end of the third rod 8331. A resilient block 8327 is formed at an end of the lower section 8325, and extends into the front opening 8324a and at a top of the third sleeve portion 8323 for anchoring the third rod 8331. A fanlike block 8328 is mounted on the lower section 8325 by a second connecting shaft 832b, and extends into a rear opening 8324b of the upper section 8324. The fanlike block 8328 forms a tooth-like surface (not labeled) thereon. A bearing portion 8326 is pivoted to the upper section 8324 by a third connecting shaft 832c. A fourth spring 8326a is provided under the bearing portion 8326. A tab 8326b is protruded from a front end of the bearing portion 8326 and locks with the fanlike block 8328. Referring to FIG. 19, the bearing portion 8326 makes the nerve hook 833 bendable in vertical.

Generally speaking, the expansion mechanism for minimally invasive operation includes outside muscle hook members 81, an inside muscle hook member 82 and a nerve hook member 83, which respectively have individual functions as following:

1. the outside muscle hook members 81 are capable of retaining (owing to the top blocks 8126) and are rotatable in diverse directions (owing to the first connectors 8122, which are omni-directionally rotatable, and the first connecting portions 8121).

2. the inside muscle hook member 82 is capable of pulling upward (owing to the pressing section 8223 and the abutting block 8224) and is free in horizontal direction (owing to the second engaging portion 8212, the pivoting shaft 8213 and the second connecting portion 8221).

3. the nerve hook member 83 is capable of retaining (owing to the resilient block 8327) and is rotatable in diverse directions (owing to the second connector 8322, which is omni-directionally rotatable, and the third connecting portion 8321). The nerve hook member 83 is further bendable (owing to the fanlike block 8328 and the bearing portion 8326).

The expansion mechanism for minimally invasive operation according to the present invention makes small incisions and hurts less tissues than prior art during minimally invasive operations. Furthermore, the present invention protects nerve, tissues from repeated stirring. Muscles can be drawn apart in the case the ligament are not removed, forming clear and relatively large operation vision.

It is understood that the invention may be embodied in other forms without departing from the spirit thereof. Thus, the present examples and embodiments are to be considered in all respects as illustrative and not restrictive, and the invention is not to be limited to the details given herein.

What is claimed is:

1. An expansion mechanism for minimally invasive lumbar operation, comprising:
    a support member including an annular guiding track;
    a plurality of sliders movably assembled on the annular guiding track;
    at least a couple of outside muscle hook members;
    an inside muscle hook member assembled on the slider; and
    a nerve hook member assembled on the slider,
    wherein each slider includes a base with an assembling portion for movably assembling on the annular guiding track, wherein stopping portions are formed on opposing sides of the base and define an elongated groove therebetween, wherein limiting portions are movably assembled to the stopping portions, and wherein a wedged groove is defined in the base, and an adjusting portion is assembled on the wedged groove.

2. The expansion mechanism for minimally invasive lumbar operation as claimed in claim 1, wherein the annular guiding track has an outer diameter of 20 cm.

3. The expansion mechanism for minimally invasive lumbar operation as claimed in claim 1, wherein the assembling portion is a lateral U-shaped slot, and wherein a slit is defined below the assembling portion for providing resilient force.

4. The expansion mechanism for minimally invasive lumbar operation as claimed in claim 1 wherein each limiting portion has a pair of latches extending upwardly, a pair of connecting bars respectively pivoting the latches to the stopping portions, wherein projections respectively extend inwardly from the latches and extend inwardly into the elongated groove, wherein each limiting portion has abutting portions depending downwardly and inclined outwardly, and wherein a first spring extends transversely through the base and has two ends respectively abutting against the abutting portions.

5. The expansion mechanism for minimally invasive lumbar operation as claimed in claim 1, wherein the adjusting portion comprises a pressing portion, a biasing portion extending upwardly from an end of the pressing portion, a pressing plate extending backward from the pressing portion, and a second spring extending into between a spring hole of the base and the pressing plate, a post extending from a distal end of the pressing plate and being wedged into a C-shaped groove in an end of the wedged groove.

6. The expansion mechanism for minimally invasive lumbar operation as claimed in claim 1, wherein each outside muscle hook member comprises a first bracket mounted on the slider, a first connecting unit connecting the first bracket, and an outside muscle hook on the first connecting unit.

7. The expansion mechanism for minimally invasive lumbar operation as claimed in claim 6, wherein a first indented surface is formed on a bottom of the first bracket for interferentially engaging with the slider, and a first engaging portion is formed at an end of the first bracket.

8. The expansion mechanism for minimally invasive lumbar operation as claimed in claim 6, wherein the first connecting unit connects with the first bracket by a versatile first connector, and wherein a first sleeve portion is formed at an end of the first connecting unit, a top block being provided on a top of the first sleeve portion, a third spring pushing the top block toward the sleeve portion, and a pivoting bar pivoting the top block toward the first connecting unit.

9. The expansion mechanism for minimally invasive lumbar operation as claimed in claim 6, wherein the outside muscle hook includes a first rod extending into the first connecting unit, and an outside hook portion at an end of the first rod.

10. The expansion mechanism for minimally invasive lumbar operation as claimed in claim 1, wherein the inside muscle hook member comprises a second bracket assembled on the slider, a second connecting unit connecting with the second bracket, and an inside muscle hook on the second connecting unit.

11. The expansion mechanism for minimally invasive lumbar operation as claimed in claim 10, wherein a second indented surface is formed on a bottom of the second bracket for interferentially engaging with the slider, and wherein a second engaging portion is formed at an end of the second bracket.

12. The expansion mechanism for minimally invasive lumbar operation as claimed in claim 10, wherein a second connecting portion of the second connecting unit connects with the second bracket by a pivoting shaft, wherein a second sleeve portion is formed at an end of the second connecting portion of the second connecting unit, wherein a pressing section is movably mounted on the second connecting portion by a pivoting lever, an abutting block being formed on an end of the pressing section and being accommodated in the second sleeve portion, and wherein a resilient element is provided between the pressing section and the second connecting portion.

13. The expansion mechanism for minimally invasive lumbar operation as claimed in claim 10, wherein the inside muscle hook includes a second rod connecting with the second connecting unit, and an inside hook portion at an end of the second rod, a toothed portion being formed on a surface of the second rod.

14. The expansion mechanism for minimally invasive lumbar operation as claimed in claim 1, wherein the nerve hook member comprises a third bracket assembled on the slider, a third connecting unit connecting with the third bracket, and a nerve hook on the third connecting unit.

15. The expansion mechanism for minimally invasive lumbar operation as claimed in claim 14, wherein a third indented surface is formed on a bottom of the third bracket for interferentially engaging with the slider, and a third engaging portion is formed at an end of the third bracket.

16. The expansion mechanism for minimally invasive lumbar operation as claimed in claim 14, wherein a third connecting portion of the third connecting unit connects with the third bracket by a versatile second connector, wherein a third sleeve portion is formed at an end of the third connecting unit, wherein an upper section extends from a top of the third sleeve portion, a front opening being defined in the upper section and communicating with the top of the third sleeve portion, a first connecting shaft extending through the front opening, wherein a lower section extends from the third connecting portion, a front end of the lower section pivoting to the front opening of the upper section, a resilient block being formed at an end of the lower section, and extending into the front opening and at the top of the third sleeve portion, and wherein a fanlike block with a tooth-like surface is mounted on the lower section by a second connecting shaft, and extends into a rear opening of the upper section, a bearing portion being pivoted to the upper section by a third connecting shaft, a fourth spring being provided under the bearing portion, a tab being protruded from a front end of the bearing portion and locking with the fanlike block.

17. The expansion mechanism for minimally invasive lumbar operation as claimed in claim 14, wherein the nerve hook includes a third rod connecting with the third connecting unit, and a nerve hook portion at an end of the third rod.

18. An expansion mechanism for minimally invasive lumbar operation, comprising:
   a support member including an annular guiding track;
   a plurality of sliders movably assembled on the annular guiding track;
   at least a couple of outside muscle hook members;
   an inside muscle hook member assembled on the slider; and
   a nerve hook member assembled on the slider,
   wherein the adjusting portion comprises a pressing portion, a biasing portion extending upwardly from an end of the pressing portion, a pressing plate extending backward from the pressing portion, and a second spring extending into between a spring hole of the base and the pressing plate, a post extending from a distal end of the pressing plate and being wedged into a C-shaped groove in an end of the wedged groove.

19. An expansion mechanism for minimally invasive lumbar operation, comprising:
   a support member including an annular guiding track;
   a plurality of sliders movably assembled on the annular guiding track;
   at least a couple of outside muscle hook members;
   an inside muscle hook member assembled on the slider;
   a nerve hook member assembled on the slider;
   wherein each outside muscle hook member comprises a first bracket mounted on the slider, a first connecting unit connecting the first bracket, and an outside muscle hook on the first connecting unit; and
   wherein the first connecting unit connects with the first bracket by a versatile first connector, and wherein a first sleeve portion is formed at an end of the first connecting unit, a top block being provided on a top of the first sleeve portion, a third spring pushing the top block toward the sleeve portion, and a pivoting bar pivoting the top block toward the first connecting unit.

\* \* \* \* \*